United States Patent
Hines

Patent Number: 6,019,784
Date of Patent: Feb. 1, 2000

[54] PROCESS FOR MAKING ELECTROFORMED STENTS

[75] Inventor: Richard A. Hines, Stilwell, Kans.

[73] Assignee: Electroformed Stents, Inc., Stillwell, Kans.

[21] Appl. No.: 08/819,757

[22] Filed: Apr. 3, 1997

Related U.S. Application Data

[60] Provisional application No. 60/014,819, Apr. 4, 1996.

[51] Int. Cl.[7] .................................. A61F 2/06; A61F 2/04
[52] U.S. Cl. .................................................. 623/1; 600/36
[58] Field of Search .................................. 623/1, 11, 12; 600/36; 606/194, 195, 198

[56] References Cited

U.S. PATENT DOCUMENTS

| | | | |
|---|---|---|---|
| 4,343,048 | 8/1982 | Ross et al. | 623/2 |
| 4,733,665 | 3/1988 | Palmaz. | |
| 5,366,504 | 11/1994 | Andersen et al.. | |
| 5,421,955 | 6/1995 | Lau et al. | 606/198 |
| 5,443,498 | 8/1995 | Fontaine. | |
| 5,443,500 | 8/1995 | Sigwart. | |
| 5,449,373 | 9/1995 | Pinchasik et al.. | |
| 5,464,419 | 11/1995 | Glastra. | |
| 5,649,952 | 7/1997 | Lam | 606/198 |

OTHER PUBLICATIONS

*The Wall Street Journal*, Ron Winslow, "J&J's 'Stent' Is Changing Coronary Care", Oct. 23, 1995, p. A8.
*Investor's NewsWire*, Thomas E. Waite, "Stent, Stents. Stents", Nov. 18, 1996.
*Investor's Business Daily*, Laura B. Benko, "Keeping The Flow Going For Heart Patients", May 24, 1996, p. A4.

*Primary Examiner*—Debra S. Brittingham
*Attorney, Agent, or Firm*—Frank B. Flink, Jr.; Stinson, Mag & Fizzell, P.C.

[57] ABSTRACT

This invention is directed to an expandable stent useful for implantation into an artery or the like. The stents are made using electroforming techniques in which an electrically-conductive mandrel is coated with a suitable resist material, after which the resist is exposed to an appropriate light pattern and frequency so as to form a stent pattern in the resist. The mandrel is then electroplated with a suitable stent material. The mandrel is etched away once a sufficient layer of stent material is deposited, leaving a completed stent.

16 Claims, 4 Drawing Sheets

PROCESS FOR MAKING ELECTROFORMED STENTS

This invention is entitled to priority due to provisional U.S. Application 60/014,819 filed Apr. 4, 1996.

The U.S. Government has rights in this invention pursuant to contract number DE-AC04-76-DP00613 with the United States Department of Energy.

BACKGROUND OF THE INVENTION

The present invention relates to a novel process for producing stents and the product of that process. More particularly, the present invention relates to a process for electroforming stents.

Expandable hollow sleeves used as intra vascular endoprosthesis, commonly called stents, are utilized as reinforcements for organ parts in a variety of situations. Typically, they are utilized to support coronary arteries after angioplasty, a process which is used to open clogged arteries. In a typical angioplasty operation, a thin flexible tube, called a catheter, is used to insert a tiny balloon, referred to as an angioplasty balloon, along an artery until it is in a desired position. Once the balloon is in position in an artery, it is inflated so as to open and enlarge the artery, after which the balloon is deflated and removed. This procedure is known to efficiently reopen clogged arteries. However, the arteries thus opened have a tendency to shrink to their former size. Stents are often utilized to hold the arteries open by mechanically supporting the inside of the artery.

A stent used for angioplasty and similar procedures typically is a small, lattice-like tubular structure, on the order of $\frac{1}{16}$ inch in diameter and $\frac{1}{2}$ inch long. The lattice which forms the tube appears like thin metal wires woven together. The tube lattice is a deformable mesh which permits expansion in the stent's radial dimension. In use, the stent is first inserted over an uninflated angioplasty balloon and then both the stent and balloon are inserted by means of a catheter into the patient. The balloon is inflated, expanding the stent and the artery, after which the balloon is deflated and removed. The expanded stent remains expanded to prevent closure of the artery.

Because of their use internal to the body, stents are subject to a number of rigorous requirements. The stent material must be biocompatible, so that it is neither absorbed by the body nor rejected by the body. Body fluids are highly corrosive to many metals. Thus the stent material must be corrosion resistant to blood and other body fluids. Also, the body's immune system attacks foreign objects. To reduce the risk of such attack, the material of the stent must be inert. The stent material also must be mechanically suitable. It must be sufficiently ductile to be deformed into an expanded condition when the balloon is inflated. It must also be sufficiently rigid to maintain its shape when the balloon is deflated and the artery or the like begins to return to its former size. Because these material constraints vary depending upon the particular application, there is a need for stents to be produced from a variety of metals. Also, blood can easily be damaged by passage through rough, irregular structures and form clots which could clog the artery. Thus, stents must have a very smooth and regular internal surface.

There are a variety of existing methods for forming these stents. In one method, stents have been made using a high power laser to machine slots in a stainless steel tube. This entails using a laser to melt away unwanted portions of the tube, forming a stent lattice. However, accurately positioning and machining a tube in this manner is difficult and the process typically requires manual inspection and processing after the laser machining is performed to remove metal fragments, commonly called slag, from the interior bore of the stent. Slag can take the form of sharp projections that can inhibit blood flow and trigger clotting. Chemical or mechanical removal of slag and inspection to insure a smooth, clean inside surface complicates the laser fabrication process and makes quality assurance and quantity production difficult.

In another method, as noted in U.S. Pat. No. 5,421,955, which is incorporated herein by reference, a mask of acid resistant material is coated onto a metal tube after which a pattern is formed in the mask by use of a laser. A stent is then formed by immersing the masked metal tube into an acid or other metal etching fluid, thus etching away the unmasked material. A limitation of this method is that the etching material eats away at portions of the tube alongside the mask-protected material, allowing the etching material to move under the mask a distance approximately equal to the tube wall thickness. As a result, the cross-section of stent elements formed by etching tends to be nonrectangular and have thin sharp edges. Further, such stents tend to have unpredictable variations in lattice pattern as a result of variations in the amount of material etched away under the mask. The sharp edges and unpredictable patterns created in this process can impede blood flow and damage the blood. Moreover, the etching process limits selection of tube materials to those amenable to etching and also limits tube selection to those with wall thickness which will accommodate the etching process.

Because of the variations inherent in existing processes for producing stents, significant amounts of post-production inspection are required to assure that the required quality is achieved. As a result, existing processes generally require substantial amounts of manual labor to produce completed stents, which results in a relatively high production cost.

SUMMARY OF THE INVENTION

It is thus an object of this invention to devise a process which is capable of producing consistently high quality stents having uniform and predictable geometry and material properties.

It is a related object of this invention to produce a stent which allows increased flexibility in selection of type of materials for forming stents along with increased flexibility in selection of stent geometry including wall thickness, length, diameter and pattern.

It is another object of this invention that stent surfaces are controlled to reduce or eliminate sharp edges and protrusions which can disrupt blood flow.

It is a related object of this invention to be able to produce stents in an efficient and reliable manner in a process suitable for quantity production at a reasonable cost.

These and other objects of the invention will be made clear from the following specification, drawings, and claims.

The present invention is a unique process for electroforming stents and the product of that process. In the basic process of the present invention, stents are formed on an appropriate sacrificial mandrel, for example copper or similar wire or tube, in a series of steps. First the mandrel is coated with a resist, which is a coating that can electrically isolate portions which it covers. The resist-coated mandrel is exposed to a light source sufficient to form a stent image on the resist, exposing portions of the mandrel. The exposed mandrel surface is then electroplated with an appropriate metal such as gold, gold alloy, or nickel to a thickness equal to the desired stent wall thickness. Subsequently, the mandrel is dissolved in an etching solution or the like leaving a completed stent.

The present invention process produces a stent in a wide variety of desirable materials and configurations. The process is suitable to provide basically any desired size of intervascular stent. Because the stent is formed on the surface of a mandrel, the interior surface is readily made very smooth. Because the present invention process uses established high accuracy imaging techniques, stents may be formed in very repeatable, controllable manner resulting in uniform and predictable stent geometry at a reasonable cost.

DETAILED DESCRIPTION OF THE PREFERRED EMBODIMENTS

The following discussions of embodiments of this invention are instructive to describe workable configurations, but are not intended to limit the scope of the invention. In particular, various materials, use of resist or photoresist, various exposure methods, number of optic fibers, and similar details which are shown in the figures and described herein are exemplary embodiments illustrative of the various configurations within the scope of the current invention. It is noted that the present invention stent manufacturing process may be implemented as either a batch process or a continuous mode process. A batch mode process is one in which a plurality of items are processed simultaneously. In a stent batch process, a plurality of individual lengths of mandrel material with multiple stent patterns may be processed simultaneously. In a continuous mode process, a plurality of parts is produced sequentially in a continuous fashion. In a continuous process of the present invention, mandrel material, such as wire, moves from a source such as a large roll of wire and is directed through a series of processing stations to continually form completed stents. The discussion below exemplifies the typical considerations of both batch as well as continuous mode processes.

Figure 1:
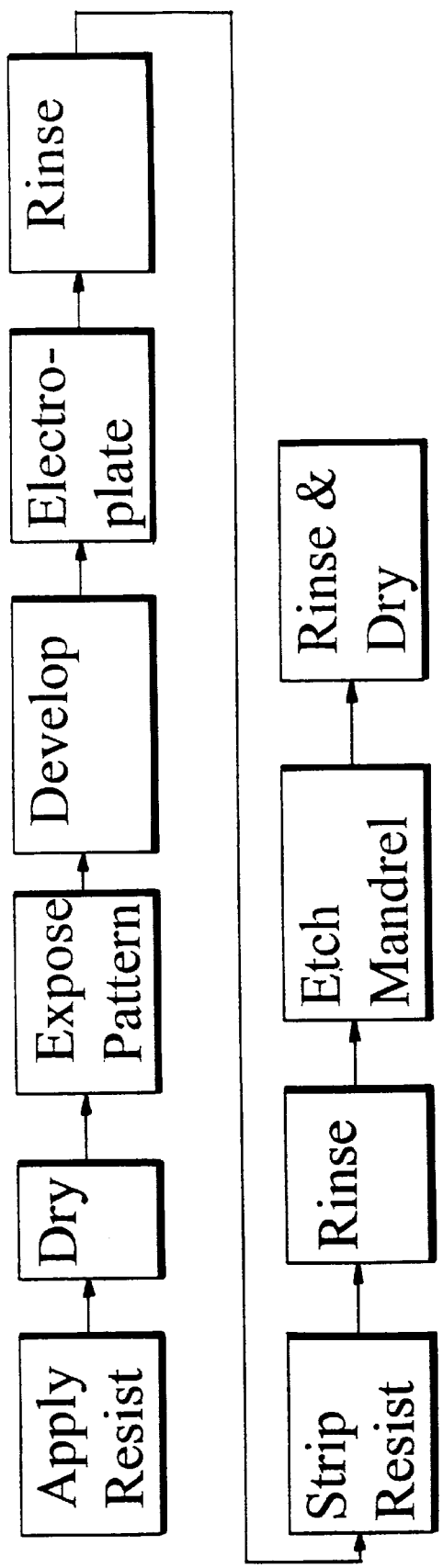
FIG. 1 is a block diagram of a preferred embodiment of a stent manufacturing process.
Figure 2:
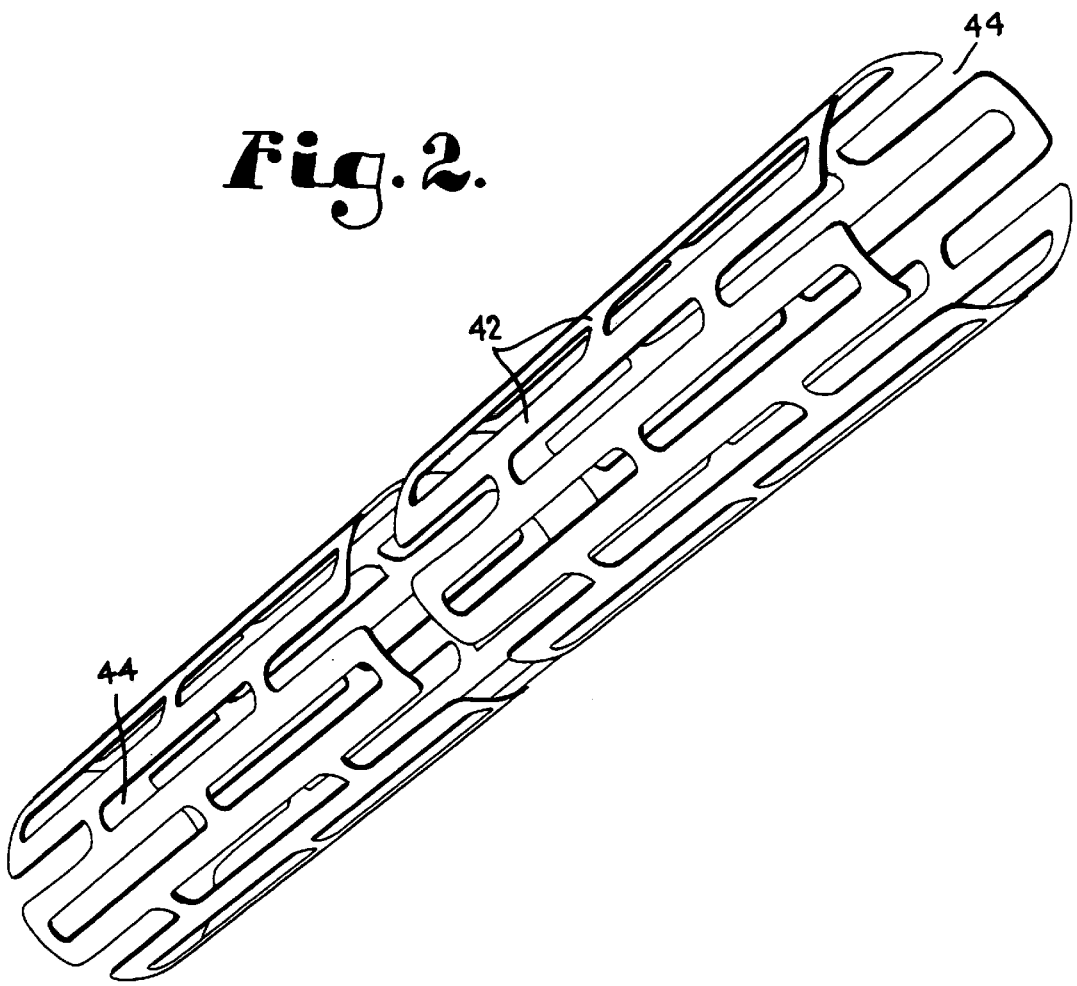
FIG. 2 is an oblique perspective view of one embodiment of a completed stent of the present invention.
Figure 3:
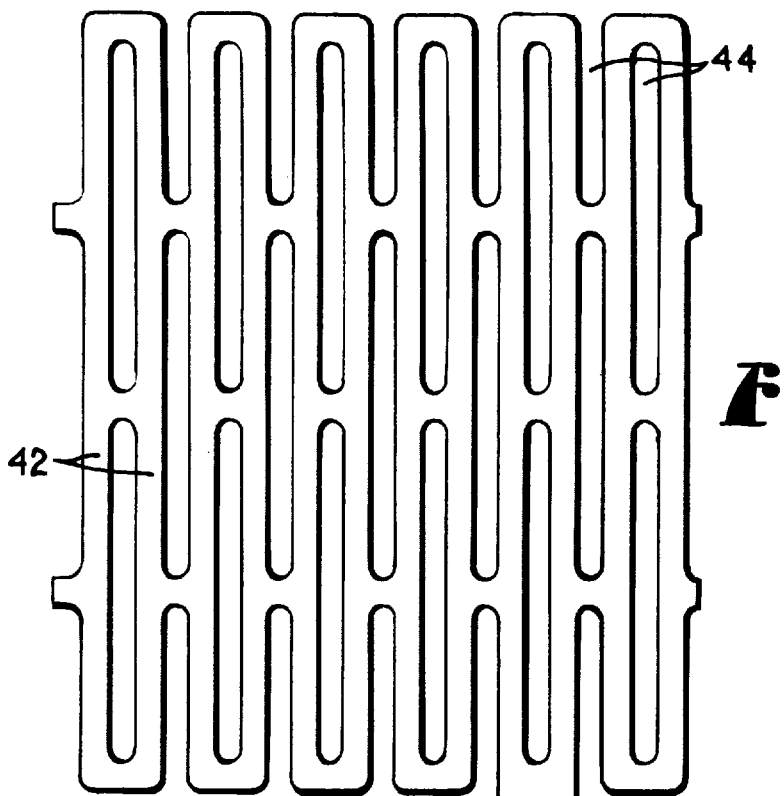
FIG. 3 is a view of a rolled out stent pattern of FIG. 2.
Figure 3:
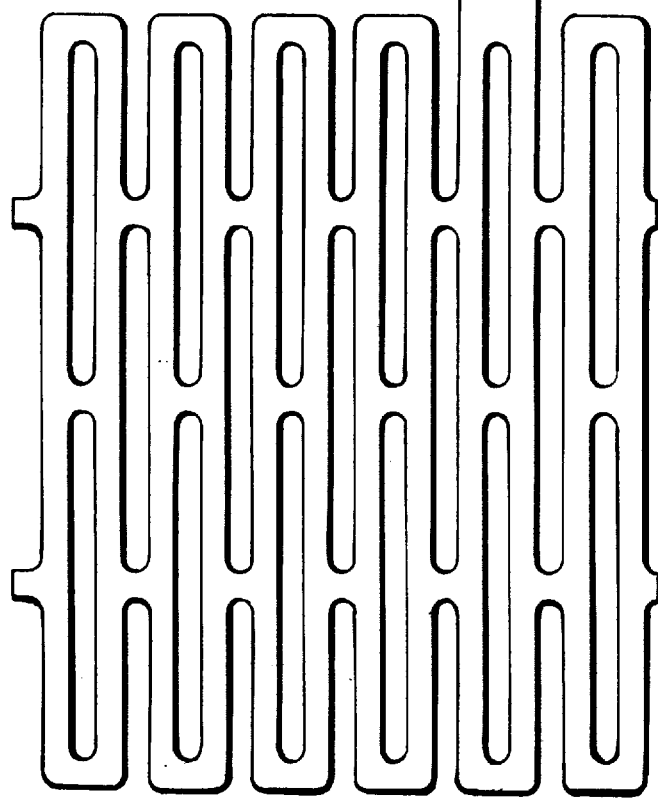

FIG. 1 shows a basic series of process steps of a preferred embodiment for producing stents according to the present invention. In this embodiment, a liquid resist which is photoimagable, called photoresist, is applied at an application station 01 to a mandrel material which is dried at a drying station 02 to form a photoimagable film on the surface of the mandrel. The photoresist-coated mandrel is then exposed to a desired stent image at an exposure station 03. FIG. 2 shows an oblique view of a typical stent image which could be formed on a mandrel. FIG. 3 shows the pattern of FIG. 2 rolled out flat for clarity. The mandrel with the exposed photoresist is passed through an appropriate chemical bath to develop the photoresist at a developing station 04. Developing of the exposed photoresist removes portions of the photoresist from the mandrel. As is known in the plating arts, depending upon the type of photoresist selected, either portions of the resist which were exposed to light are removed or, alternatively, portions of the resist which were not exposed are removed. Either type of resist is suitable for the present invention. Thus, after the photoresist is developed, the desired stent material is electroplated onto exposed portions of the mandrel at a plating station 05. Thickness of the stent thus electroplated is controlled by factors well known in the electroplating arts. Following electroplating, the electroplate solution is rinsed off of the mandrel and stent at a rinsing station 06. Next the remaining photoresist is removed (stripped) at a stripping station 07 by an appropriate chemical after which the mandrel and stent are rinsed at station 08 to remove photoresist stripping chemicals. The mandrel is removed by dissolving it in an appropriate etching solution at etching station 09, after which the completed stent is rinsed and dried at station 10.

Figure 4:
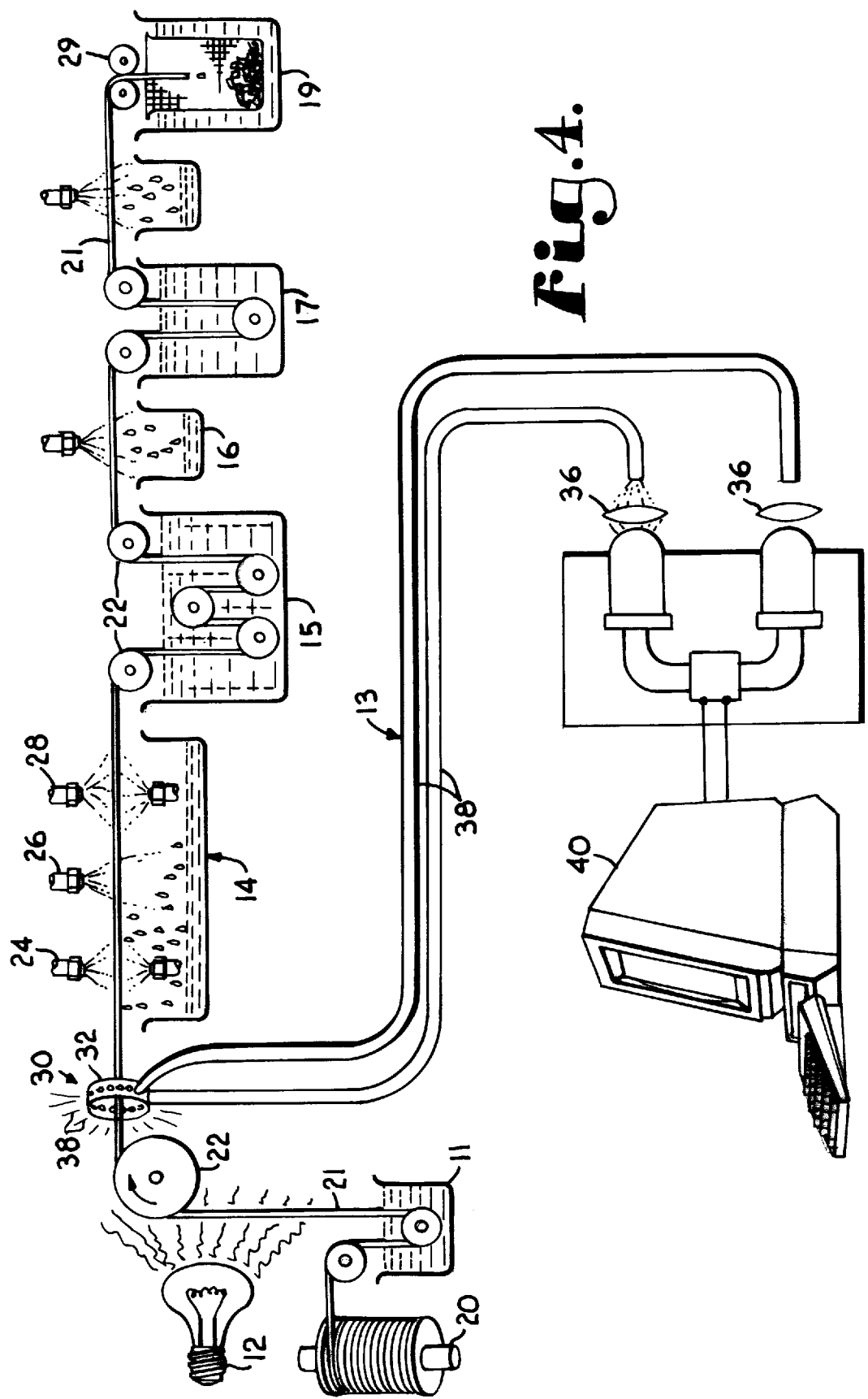
FIG. 4 is a pictographic block diagram of a preferred embodiment of a continuous mode stent manufacturing process.

FIG. 4 shows a pictographic representation of a preferred embodiment of the present invention process which includes features allowing production of stents in a continuous mode process. For clarity, items which serve functions similar to stations 01 through 09, respectively shown in FIG. 1, are numbered 11 through 19 in FIG. 4. In this embodiment, a roll 20 containing wire or tube with suitable characteristics as discussed herein to be used as a mandrel is configured so that a continuous length of the mandrel 21 may be pulled from the roll 20. The mandrel 21 is trained over rollers 22 and caused to pass through a tank of liquid photoresist 11. Next, the resist-coated mandrel 21 is moved past a heat lamp 12 or similar drying device and then past an exposure system 13, and through a resist development tank 14. The development tank contains a developing spray 24, a rinsing spray 26, and a drying station 28. At this point, the resist coating on the mandrel 21 has been removed selectively from the areas where plating is to occur. The mandrel 21 next passes through a plating tank 15, where the desired stent material is plated. The plated mandrel 21 then moves through a rinse spray 16, a resist strip tank 17, another rinse spray 18, and into an etch tank 19 where the mandrel 21 is dissolved. The completed stents collect in the etch tank 19 and are subsequently removed for rinsing and drying. The mandrel 21 preferably is pulled at a constant speed by pinch rollers 29 driven at the same speed as other rollers in the process. The time the mandrel is at each processing station (e.g., drying and electroplating) may readily be controlled by adjusting the length of mandrel portion at a given station or tank. The preferred exposure system 13 of this embodiment comprises a controller 40, which may be a computer or similar device, operably connected to light emitting diodes (LEDs) 36 that are coupled to optic fibers 38. The optic fibers 38 are routed to a mounting fixture 32. The optic fibers 38 and fixture 32 together form an exposure ring 30 which surrounds the mandrel. The optic fibers 38 are used to direct light to the resist coating on the surface of the mandrel 21 and thereby create a stent pattern in the resist.

Stent material is selected for biocompatibility and mechanical characteristics. It must be sufficiently ductile to be radially expandable to form an appropriate intra vascular endoprosthesis and sufficiently rigid to hold its shape once the expansion force is removed. It must also be sufficiently inert to be biocompatible and resistant to etching solutions. Gold and various gold alloys generally satisfy these requirements because they are generally inert and resistant to corrosion from bodily fluids and, also are resistant to a wide variety of etching solutions. Generally any electroplatable materials could be formed into stents in the present invention process. Other metals which have specific beneficial characteristics as stent materials include silver, nickel, platinum, rhodium, palladium, iron and various alloys of these metals. It is anticipated that high gold, platinum, or nickel content alloys with from about 95 to about 100 percent content of such metals would produce stents with highly desirable characteristics. Selection of particular materials for a specific application would be based primarily upon biocompatibility and mechanical characteristics as discussed herein. Specialized materials, such as radioactive isotopes, may also be incorporated into the present invention stent to gain specific medical benefits. Radioactive isotopes have been shown to reduce blood clotting. Such materials may either be incorporated into the original electroformed stent or the completed stents could be electroplated with additional layers of material to change the final mechanical and/or medical characteristics of the stent. The stents may also be coated with an inert organic coating to isolate the stent from the body chemistry. Thus, it may be seen that the present invention process allows great latitude in the selection of desirable stent materials and characteristics.

Mandrel material selection is influenced by the availability of etchants that could dissolve the mandrel without damaging the selected stent material. Conductivity, ductility, and compatibility with the electroplating process also influence mandrel material selection. For example, in applications in which gold or gold alloys are used as stent materials, a wide range of materials are suitable for mandrel material because of gold's resistance to a wide variety of etchants. Copper is a preferred mandrel material because it is highly conductive, is easily electroplated, and is commercially available in a wide variety of manufactured wire and tube sizes. In comparison, if nickel is selected as a stent material, aluminum would be a more preferred mandrel material than copper because aluminum can be more easily be selectively dissolved in the presence of nickel than can copper. Thus, various materials could be utilized to form the mandrels of the present invention process based upon parameters familiar to one skilled in the art. Basically, any sufficiently ductile and electrically conductive material which is acceptable as an electroplating base material that can be easily etched away from the electroformed stent could be utilized. Thus, usable materials include copper, aluminum, nickel, steel, and the like. The preferred shape of a mandrel will generally be circular to best form a circular stent, although it would be readily apparent to one skilled in the art that a variety of other shapes could be made by the present invention process. In one embodiment of the present invention, a balloon catheter may be directly used as a mandrel. In this embodiment, the catheter is prepared by coating it with an appropriate electroconductive material. Using the steps of the present invention process, stents then may be directly electroplated on the balloon catheter.

Two basic types of resist material are suitable for use in this invention, i.e., photoimageable resist, called photoresist and resist which is not photoimagable, which will be referred to as nonphotosensitive resist. As used herein, the term resist refers to a substance which is used to form a dielectric layer to prevent electroplating of materials and which may be selectively removed. In use, photoresist is exposed to an appropriate frequency and pattern of light and, then, developed. Portions of the mandrel area to be electroplated are uncovered by the developing process. Photoresist generally is the preferred resist material for use in the present invention process, because of its commercial availability and ease of use. As discussed herein, there are a number of photoimaging systems available for use with photoresist. Nonphotosensitive resists may also be utilized in the present invention. In using nonphotosensitive resist, a high intensity laser light is used to ablate the resist in order to expose the mandrel. Although such systems are feasible, generally it is more difficult to control and implement high intensity imaging systems as compared to low intensity systems. The particular resist or photoresist selected must be compatible with the selected mandrel, plating baths and, also, must be compatible with the exposure methods to be utilized.

A variety of methods could be used to expose the stent image on the photoresist coated mandrel. One preferred embodiment of an exposure method is shown pictographically in FIG. 4. In this embodiment, a plurality of optical fibers 38 are used to direct light to an exposure ring 30, through which ring a photoresist-coated mandrel 21 is passed. The exposure ring includes a mounting fixture 32 on which a plurality of optic fibers 38 or other light-conducting members are mounted. The exposure ring advantageously is located in a plane perpendicular to the axis of the mandrel 21. The optic fibers 38 are mounted in a spaced relation around the periphery of the mounting fixture 32 and are configured to direct light toward the center of the ring onto the mandrel 21. In this manner, a stent pattern can be exposed on a moving mandrel by selectively passing light through the multiple optic fibers 38 to create a stent pattern. For example, 24 optic fibers evenly spaced around an exposure ring 30 would each cover $\frac{1}{24}$ of the circumference of the mandrel or 15 degrees of arc. By controlling light from each fiber at the appropriate time while the mandrel is moved, a stent image with 24 alternating bars and spaces, such as is shown in FIGS. 2 and 3, could be exposed on the surface of the mandrel.

Optic fibers for exposing the resist need not be located in one plane along the axis of the mandrel. Rather, optic fibers may be staggered along the travel of the mandrel and, by switching the light to individual fibers on or off at the appropriate time as the mandrel passes, the entire outer surface of the mandrel may be exposed. In another embodiment, bundles of smaller fibers may be used to provide a line source of light, which may advantageously be used to expose large sections of mandrel simultaneously. Further, bundles of small optic fibers provide a more uniform light than a single circular light from a single fiber. Alternatively, fibers or light pipes with noncircular cross sections may be used to produce a variety of light and exposure patterns. For example, a narrow rectangular cross section at the exit end of an optic fiber approximates a line source which produces uniform light density and, thus, uniform exposure. In comparison, a larger rectangular cross section at the exit end of a fiber may be used to flash expose larger areas of a stent pattern. Similarly, a tapered filament or light pipe may be used to funnel light from a large entrance to a small exit area, concentrating available light to accelerate exposure.

As is depicted in FIG. 4, one preferred light source consists of an appropriate number of light emitting diodes (LEDs) 36, each with an associated optic fiber or fiber bundle 38 to bring light to the photoresist-coated surface of the wire mandrel. Because LEDs may rapidly be cycled on and off electronically, computer control of amplified signals to power LEDs at the appropriate times may be used to trace the stent pattern on the moving mandrel. Another option for light sources is low power lasers. Such lasers with a wavelength output appropriate for exposing the photoresist could be used to directly expose the photoresist or could be used to inject light into each fiber or bundle of fibers 38. An exposure system using lasers in place of LEDs would be capable of very high writing speeds (stents exposed per unit of time) because the higher intensity of the light available from such lasers exposes photoresistive materials more rapidly than lower intensity sources, such as LEDs. In another embodiment, an optical fiber exposure system uses a continuous light source, such as a high pressure mercury vapor lamp with optical fibers and mechanical shutters to generate light at the appropriate area and time in the appropriate fiber to expose the stent pattern.

Various other exposure methods are known in the art that readily could be used in the present invention process. For example, a cylindrical photomask may be used with a flash lamp exposure to form an image of a stent on a photoresist-coated mandrel. After each image is thus formed, the mandrel is indexed to the next unexposed section of mandrel. Thus, using intermittent linear motion of the mandrel, stent images are produced along the length of the mandrel in the photoresist.

As noted herein, FIGS. 2 and 3 depict a standard stent pattern such as is known in the art. The stent pattern shown can readily be made from the 24 optic fiber exposure system discussed above. FIGS. 2 and 3 show 24 bars 42 and spaces 44 around the circumference of the stent. Thus, the pattern shown may simply be made by selectively operating LEDs or the like as a resist-coated mandrel is moved past an exposure ring 30. As is apparent to one skilled in the plating arts, the present invention process can be used to produce virtually any stent pattern desired by using the various exposure systems available.

Development of the exposed photoresist is accomplished by passing the exposed resist-coated mandrel through a developer solution. The developer solution may readily be applied either as a spray or a dip. The type of developer solution and process time depends upon the particular photoresist selected. Generally stated, there are a large number of liquid photoresist coatings and related developers available which may be utilized in the present invention.

References to plating herein are to various established electroplating techniques and substances that may be employed in this invention. As is known to one skilled in the plating arts, plated metal thickness is proportional to time in the plating bath and plating electrical current. Plating current may be manually or automatically adjusted to control the desired stent thickness. In a continuous mode process an appropriate thickness control system is used to monitor the plated thickness and automatically adjust the plating current. Alternating or pulsed plating currents may be used to improve or modify the deposit properties. If an alloy is being deposited, the alloy composition is a function of the current density. Time-based changes in the current density can produce radial microscopic changes in alloy composition, which may be desirable to meet various strength and corrosion resistance requirements. Various alloys have characteristics which are desirable for stents. For example, high gold-content alloys can be produced by electroplating techniques. Such alloys have high strength and are essentially as inert as gold. Therefore, these alloys also are expected to be biocompatible.

After plating, the mandrel is dissolved in an appropriate etchant. For example, nitric acid or a ferric chloride solution is suitable for removing copper from gold stents and sodium hydroxide solution is suitable for removing aluminum from nickel stents. Various other etching solutions are available to one experienced in the electroplating arts for various mandrel and stent material combinations.

When the mandrel material dissolves, the individual stents may be collected in a variety of fashions such as in a basket contained in the etchant tank, or onto a moving belt. The completed stents preferably are rinsed to remove etchant solution.

From the foregoing, it will be seen that this invention is well-suited to attain all the ends and objects set forth herein together with other advantages which are obvious and inherent to the invention.

It will be understood that certain features and combinations are of utility and may be employed without reference to other features and combinations. This is contemplated and within the scope of the invention.

Since many possible embodiments may be made of the invention without departing from the scope thereof, it is to be understood that all matters herein set forth or shown in the accompanying drawings are to be interpreted as illustrative and not in a limiting sense.

I claim:

1. A process for producing a stent by electroforming comprising the steps of:
   coating a mandrel with a resist;
   exposing portions of said resist to a light pattern so as to form a stent pattern on said mandrel in said resist;
   plating metal onto said mandrel in said stent pattern so as to form a stent; and
   dissolving said mandrel.

2. A process as claimed in claim 1 wherein said resist is photosensitive and comprising the additional step of:
   developing said resist subsequent to the step of exposing portions of said resist.

3. A process as claimed in claim 2 wherein said plating metal is an alloy comprising from about 95 to about 100 percent of a metal selected from the group consisting of gold, platinum, and nickel.

4. A process as claimed in claim 2 wherein said plating metal is an alloy comprising metal selected from the group consisting of gold, platinum, nickel, iron, silver, rhodium, and palladium.

5. A process as claimed in claim 2 in which said mandrel is a metal selected from the group consisting of copper and aluminum.

6. A process as claimed in claim 2 in which said mandrel is an angioplasty balloon.

7. A process as claimed in claim 2 wherein said plating metal is a first metal, further comprising the step of plating a second metal onto said stent subsequent to the step of removing said mandrel.

8. The product of the process as claimed in claim 2.

9. A process as claimed in claim 2 wherein the step of exposing portions of said resist to a light pattern consists of conducting light produced by light-emitting diodes through optical fibers so as to expose said stent image in said photoresist and wherein said optical fibers have output ends which are constrained in a ring configuration, said ring defining a center, and which output ends are positioned so as to focus light at the center of said ring.

10. The product of the process as claimed in claim 9.

11. A process as claimed in claim 1 wherein the step of exposing portions of said resist to a light pattern consists of selectively removing resist with a laser to form said stent pattern.

12. A process for producing a stent by electroforming comprising the steps of:
   coating an electrically-conductive mandrel, which mandrel has an exterior surface, with a resist material which is photosensitive onto said exterior surface;
   exposing portions of said resist material to a light pattern so as to form a stent pattern on said mandrel in said resist;
   developing said resist material so as to expose a stent pattern on said exterior surface of said mandrel;

plating metal onto said mandrel in a stent pattern to form a stent; and dissolving said mandrel.

13. A process as claimed in claim 12 wherein said plating metal is an alloy comprising from about 95 to about 100 percent of a metal selected from the group consisting of gold, platinum, and nickel.

14. A process as claimed in claim 12 wherein said plating metal is an alloy comprising metal selected from the group consisting of gold, platinum, nickel, iron, silver, rhodium, and palladium.

15. A process as claimed in claim 14 wherein the step of exposing portions of said resist to a light pattern consists of conducting light produced by light-emitting diodes through optical fibers so as to expose said stent image in said resist and wherein said optical fibers have output ends which are constrained in a ring configuration, said ring defining a center, and which output ends are positioned so as to focus light at the center of said ring.

16. The product of the process as claimed in claim 14.

* * * * *